(12) United States Patent
Albers

(10) Patent No.: US 10,610,147 B2
(45) Date of Patent: Apr. 7, 2020

(54) NEURODEGENERATIVE DISEASE SCREENING USING AN OLFACTOMETER

(71) Applicant: The General Hospital Corporation, Boston, MA (US)

(72) Inventor: Mark W. Albers, Charlestown, MA (US)

(73) Assignee: The General Hospital Corporation, Boston, MA (US)

( * ) Notice: Subject to any disclaimer, the term of this patent is extended or adjusted under 35 U.S.C. 154(b) by 256 days.

(21) Appl. No.: 15/512,541

(22) PCT Filed: Sep. 18, 2015

(86) PCT No.: PCT/US2015/050957
§ 371 (c)(1),
(2) Date: Mar. 17, 2017

(87) PCT Pub. No.: WO2016/044734
PCT Pub. Date: Mar. 24, 2016

(65) Prior Publication Data
US 2017/0290541 A1    Oct. 12, 2017

Related U.S. Application Data

(60) Provisional application No. 62/052,845, filed on Sep. 19, 2014.

(51) Int. Cl.
*A61B 5/00* (2006.01)
*G06F 17/40* (2006.01)
(Continued)

(52) U.S. Cl.
CPC .......... *A61B 5/4011* (2013.01); *A61B 5/4082* (2013.01); *A61B 5/4088* (2013.01);
(Continued)

(58) Field of Classification Search
CPC ... A61B 5/4011; A61B 5/4082; A61B 5/4005; A61B 5/4088; A61B 5/4076;
(Continued)

(56) References Cited

U.S. PATENT DOCUMENTS

2007/0077204 A1* 4/2007 Devanand .............. A61K 49/00
424/9.2

OTHER PUBLICATIONS

Schriever, Valentin et al., "A computer-controlled olfactometer for a self-administered odor identification test", Jan. 3, 2011, Eur Arch Otorhinolaryngol, 268:1293-1297 (Year: 2011).*

(Continued)

*Primary Examiner* — Matthew Kremer
*Assistant Examiner* — Avery M Foley
(74) *Attorney, Agent, or Firm* — Quarles & Brady LLP

(57) ABSTRACT

Systems and methods of the present invention provide for an olfactometer for delivering one or more odors and one or more computing devices configured to: receive user input for an odor memory test and an odor discrimination test; calculate a score for the odor memory test and the odor discrimination test; calculate a first and second confidence interval threshold and a second confidence interval threshold for a first and second predicted odor memory score respectively, based on a relationship between, respectively, the odor memory test score and odor discrimination test score, and previously-entered performance data queried from the database; and responsive to the score for the odor memory test not being greater than the first confidence interval threshold and the score for the odor discrimination test not being greater than the second confidence interval threshold, generate a report identifying a user as high risk for a neurodegenerative disease.

19 Claims, 10 Drawing Sheets

(51) Int. Cl.
  *G16H 40/63*     (2018.01)
  *G16H 50/20*     (2018.01)
  *G16H 50/30*     (2018.01)
  *G16H 15/00*     (2018.01)

(52) U.S. Cl.
  CPC .......... *A61B 5/7275* (2013.01); *A61B 5/7475* (2013.01); *G06F 17/40* (2013.01); *G16H 40/63* (2018.01); *G16H 50/20* (2018.01); *A61B 5/0022* (2013.01); *G16H 15/00* (2018.01); *G16H 50/30* (2018.01)

(58) Field of Classification Search
  CPC ... A61B 5/7275; A61B 5/7271; A61B 5/7475; A61B 5/0022; G06F 17/40; G06F 19/00; G16H 50/20; G16H 40/63
  See application file for complete search history.

(56) References Cited

OTHER PUBLICATIONS

Parr, Wendy et al., "Demystifying Wine Expertise: Olfactory Threshold, Perceptual Skill and Semantic Memory in Expert and Novice Wine Judges", 2002, Chem. Senses, 27:747-755 (Year: 2002).*

OLFACT-C: User Manual; Revision 2.1 (Jul. 2012); http://www.osmicenterprises.conn/docs/OLFACT-C_User_Manual_8-12-13.pdf (Year: 2012).*

International Search Report and Written Opinion dated Dec. 15, 2015 for International Application PCT/US2015/050957.

Wallace; D et al. Determination of the olfactory threshold using a piezoelectric microdispenser for neurodegenerative disease diagnostics. Meas. Sci. Technol. Oct. 19, 2006, vol. 17: pp. 3102-3109. [Retrieved from the Internet]: <URL:http://microfab.com/images/papers/mst6_ 11_031.pdf> <DOI:10.1088/0957-0233/17/11/031 >. p. 1, abstract; p. 2, figure 1, col. 2, paragraphs 3 & 4; p. 4, col. 1, paragraph 2; p. 6, col. 2, paragraph 1.

Schriever, V et al. A computer-controlled olfactometer for a self-administered odor identification test. Eur Arch Otorhinolarynaol. Apr. 3, 2011, 268: pp. 1293-1297. [Retrieved from the Internet]: <URL: http://link.springer.com/article/10.1007%2Fs00405-011-1593-z> <DOI10.1007/s00405-011-1593-z>. p. 2, col. 1, paragraph 3, col. 2, paragraph 2, table 1 & figure 1; p. 3, col. 1, col. 2, paragraph 1, figures 2(a), (b), (c), (d), (e).

Albers, A et al. Perception of Odor Episodic Memory (POEM) test as a candidate biomarker for early Alzheimer's disease. Alzheimer's & Dementia. Jul. 2013, vol. 9: pp. P199 . Retrieved from the Internet: <URL: http://www.sciencedirect.com.libproxy.txstate.edu/science/article/pii/S 1552526013010133?> <DOI:10.1016/j.jalz.2013.05.356>. p. 4, col. 1, p. 1-134.

Sense of smell in the detection of Alzheimer's Disease. Audio Transcript [online]. ABC Radio National, Dec. 9, 2013 [retrieved on Nov. 12, 2015]. (Retrieved from the Internet): <URL: http://www.abc.net.au/radionational/programs/healthreport/sense%ADOf%ADsmell%ADin%r ADthe%ADdetection%ADof%ADalzheimer27s%ADdisease/5144070#transcript>. p. 1, paragraph 1; p. 2, paragraphs 2-4.

Osmic Enterprises, Inc., OLFACT-C ("Combo" (RL, ID20, Memory)), 25 pages, 2012, Product Manual.†

Frank, Rybalsky, Brearton & Mannea, Odor Recognition Memory as a Function of Odor-Naming Performance, 13 pages, 2010, Chem. Senses, vol. 36: 29-41; 2011.†

Cessna & Frank, Does Odor Knowledge or an Odor Naming StrategyMediate the Relationship Between Odor Naming and Recognition Memory?, 9 pages, 2013, Chem. Percept., 6:36-44; 2013.†

Hastings & Knauf, The OLFACT (Olfactory Function Assessment by Computerized Testing) Test Battery; Poster and List of Abstracts from 15th Annual International Symposium on Olfaction and Taste, 3 pages, 2008, Chem. Senses, 33:S1-S175; 2008.†

Hastings & Wilson, Clinical Test of Olfaction Based Upon a MEMS-Microvalve Olfactometer; Poster and List of Abstracts from the 26th Annual Meeting of the Association for Chemoreception Sciences, 3 pages, 2005, Chem. Senses, 30: 265-278; 2005.†

Hastings, Regulatory Approval for the Olfact Test Battery; Project No. 5R44DC006369-06, 2 pages, 2011, NIH Reporter.†

Hastings, A Clinical Test of Olfaction Based Upon MEM-Microvalves; Project No. 5R44DC006369-03, 2 pages, 2007, NIH Reporter.†

\* cited by examiner
† cited by third party

```
File  Edit  Tools        ⇐ ⇒

Username: [        ]    Password: [        ]

Percepts of Odor Episodic Memory (POEM)/Odor Percept Identification Test (OPID-
20)

Prepare to sniff ...

Did you smell this odor in the last test?   | Yes  ▽ |
                                            | No     |

[Cued subsequent to response]
Can you name this odor?
                             | a - banana      ▽ |
                             | b - garlic        |
                             | c - cherry        |
                             | d - baby powder   |
```

```
File  Edit  Tools         ⇐ ⇒
```

Username: [        ]   Password: [        ]

Odor Discrimination Test (OD)

Prepare to sniff ...

[Cued subsequent to first odor]

Prepare to sniff ...

[Cued subsequent to second odor]

Were the two presented odors the same or different?   | The same ▽ |
                                                      | Different  |

NEURODEGENERATIVE DISEASE SCREENING USING AN OLFACTOMETER

CROSS REFERENCE TO RELATED APPLICATIONS

This application represents the national stage entry of PCT/US2015/050957, filed Sep. 18, 2015, which claims benefit of U.S. Provisional Patent Application 62/052,845 filed Sep. 19, 2014, which is incorporated in its entirety by reference, herein.

FIELD OF THE INVENTION

The present invention generally relates to the field of screening tests used for detecting neurodegenerative diseases, and specifically to administering screening tests via an olfactometer and generating results via the disclosed system.

BACKGROUND OF THE INVENTION

Recent converging evidence indicates that neurodegenerative diseases, including Alzheimer's and Parkinson's disease, are present a decade or more prior to the onset of clinical symptoms. This preclinical period is thought to be more amenable to therapeutic intervention. Detection of individuals and means to follow progression of neurodegenerative disease are major impediments to the development of therapies for this preclinical period. The olfactory neural system is vulnerable to these disease pathologies and a functional screen of smell identification (e.g, the University of Pennsylvania Smell Identification Test (UPSIT)) has been shown to be abnormal in individuals with dementia and mild cognitive impairment. However, concerns over specificity (other reasons to have an olfactory deficit) have precluded broad adoption of these methodologies. The validation of indices to identify cognitively healthy individuals at risk for developing the progressive memory symptoms of neurodegenerative diseases, and to follow these individuals over time is essential for conducting therapeutic trials in this preclinical phase.

There are numerous systems and methods for trying to diagnose neurodegenerative diseases, including countless imaging techniques, field tests for memory and motor skills, etc. All are plagued by subjective evaluation criteria and inherent limitations on the "maturity" required of the neurodegenerative disease before a diagnosis can be made. Of course, it is well documented that the long-term prognosis and quality of life is increased greatly the earlier that the diagnosis can be made. Of course, early detection in all these systems and methods stands in direct opposition to the certainty of diagnosis. As such, much better systems and methods are needed.

SUMMARY OF THE INVENTION

The present invention provides an olfactometer for delivering one or more odors and one or more computing devices configured to: receive user input for an odor memory test, an odor identification test, and an odor discrimination test; calculate a predicted score for the odor memory test based on the odor identification test and calculate a second predicted odor memory score based on the odor discrimination test; calculate a confidence interval thresholds for each predicted odor memory score based on the relationship between the odor memory test score and the odor identification score as well as the odor memory test score and odor discrimination test score, respectively, and previously-entered performance data queried from the database; and responsive to whether the measured score for the odor memory test falls below the confidence interval thresholds for both the odor discrimination and odor identification test, generate a report identifying a user as high risk for a neurodegenerative disease.

The above features and advantages of the present invention will be better understood from the following detailed description taken in conjunction with the accompanying drawings.

DETAILED DESCRIPTION

Figure 1:
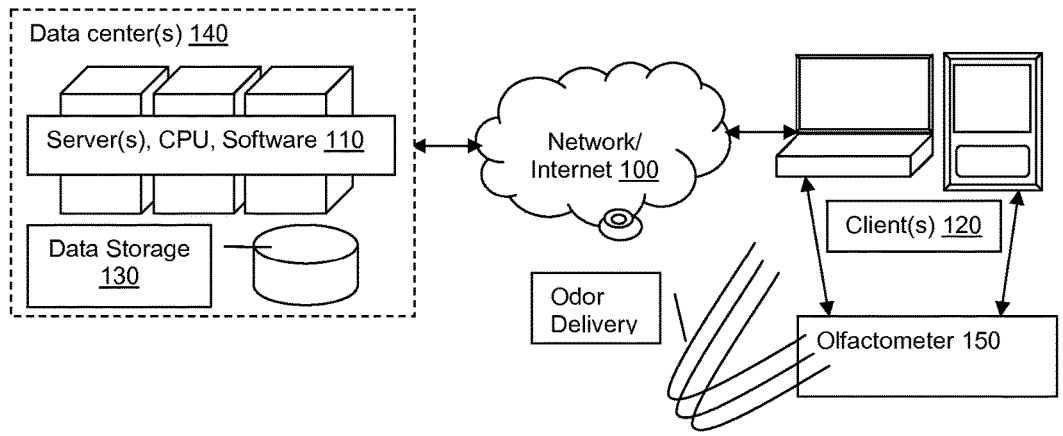
FIG. 1 illustrates a system for screening neurodegenerative diseases using an olfactometer.

The present invention will now be discussed in detail with regard to the attached drawing figures that were briefly described above. In the following description, numerous specific details are set forth illustrating the Applicant's best mode for practicing the invention and enabling one of ordinary skill in the art to make and use the invention. It will be obvious, however, to one skilled in the art that the present invention may be practiced without many of these specific details. In other instances, well-known machines, structures, and method steps have not been described in particular detail in order to avoid unnecessarily obscuring the present invention. Unless otherwise indicated, like parts and method steps are referred to with like reference numerals.

The present disclosure provides a new olfactory paradigm that has promise to detect and follow individuals at risk for neurodegenerative disease. It is non-invasive and inexpensive relative to positron emission tomography (PET) imaging, magnetic resonance imaging (MRI), and lumbar puncture, and other current methods that are in intense development.

Figure 2:
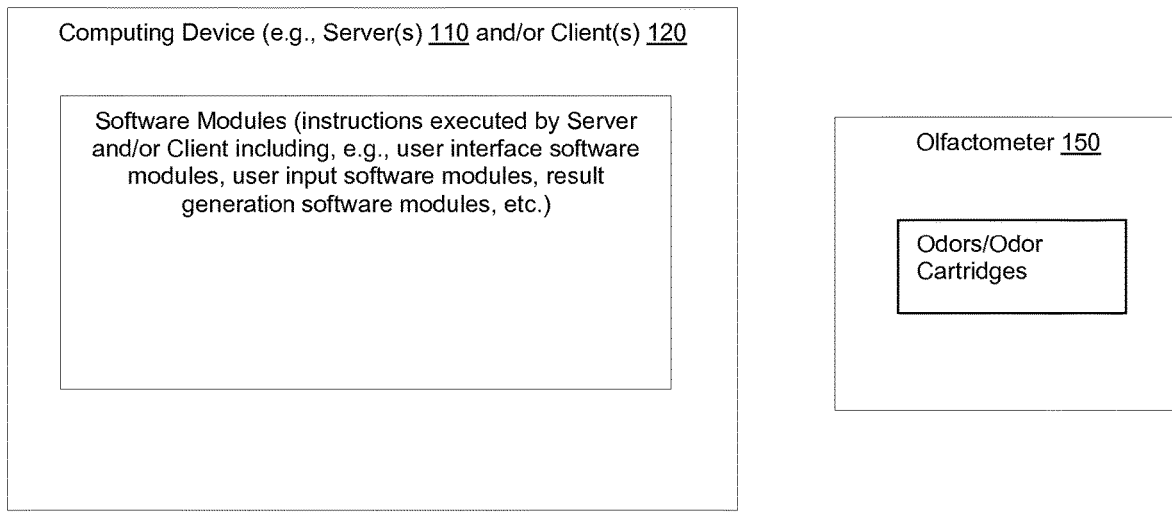
FIG. 2 illustrates a more detailed system for screening neurodegenerative diseases using an olfactometer.

FIGS. 1 and 2 show a hardware and software environment in accordance with the present disclosure in which the tests may be given and the results calculated. As seen in FIGS. 1 and 2, this environment may include an olfactometer 150 coupled to a client computer 120 as described below. One or more processors on a combination of one or more computing devices (possibly server computer(s) 110 and/or client computing machines 120) may interact in a networked environment, possibly via the one or more computing devices 120 communicatively coupled to a network 100. The processor(s) may execute instructions, possibly compiled and executable software code that, when executed by the processor, causes the processor to execute the algorithms and method steps described below for administering the tests and calculating results. The server(s) 110 and/or client(s) 120 may execute the disclosed algorithms to calculate and display the results of the tests to the user, test subject and/or patient. Data used for these calculations, as well as the results of these calculations, may be queried from and/or stored within a database 130, which may be communicatively coupled to the network 100, the server 110 and/or the client 120.

The olfactometer 150 may include a variety of instruments used to detect odors and measure a user, test subject or patient's ability to identify odors. The olfactometer 150 may be used in conjunction with human subjects in laboratory or other settings, to quantify and qualify human olfaction and/or to gauge the odor detection threshold of substances. As a non-limiting example, an olfactometer 150 may include a portable OLFACT olfactometer produced by Osmic Enterprises of Cincinnati, Ohio.

The currently-predominant test used as a functional screen of smell identification in the field is the scratch and sniff smell identification test. The olfactometer may be designed to mimic this test, using, for example, odors based on the originally administered scratch and sniff tests. The tests described below may use multiple odors (e.g., 20 different odors—i.e., menthol, clove, leather, strawberry, lilac, pineapple, smoke, soap, grape and lemon for an odor recognition test and additionally, banana, garlic, cherry, baby powder, grass, fruit punch, peach, chocolate, dirt, and orange to be compared in an odor memory test), a combination of which may be delivered to the user, test subject and/or patient. In some of these tests, it is important that the subject be able to distinguish between odors. Thus, the olfactometer 150 may be configured to accept these odors via a dedicated line for the delivery of each odor to the user, in order to prevent cross-contamination.

In some configurations, the olfactometer may include scented cartridges or odor packs (for example, as may be provided by a commercial fragrance house or the producer of the olfactometer) that are used to generate the odors delivered to the subjects during the tests. Although 20 specific odors are listed above, the olfactometer 150 may be configured to accept cartridges for a wide variety of odors created, and may be used in the tests accordingly. For example, tests may be configured to accept artificial flavorings that are common within the United States (e.g., artificial grape or strawberry flavor). The fragrance house providing the cartridges for the olfactometer 150 may also provide odors from the actual fruits themselves, as opposed to the artificial flavor. This would be especially useful for international applications of the disclosed invention, where foreign countries would not recognize artificially created odors familiar only to US residents. Furthermore, the fragrance house may create odors for the tests that are specific to a specific region or culture.

The olfactometer 150 may be coupled with one or more software modules that both drive the olfactometer and allow the algorithms and method steps below to be implemented without requiring a clinician to have knowledge how to do so. The one or more software modules may run on a client machine 120, which may include a computer or program that provides services to other computers, programs, or users either in the same computer or over a computer network 100. As non-limiting examples, the client 120 may include a laptop computer, a desktop computer or a mobile device, such as a mobile phone or a tablet computing device, which may connect wirelessly to the olfactometer 150.

The client 120 may include a user interface allowing the user/subject/patient to interact with the tests and display the results of the tests to the user. This user interface may include graphical, textual, scanned and/or auditory information a computer program presents to the user, and the control sequences such as keystrokes, movements of the computer mouse, selections with a touch screen, scanned information etc. used to control the program. The commands received within the software modules, or other data, may be accepted using a field, widget and/or control used in such interfaces, including but not limited to a text-box, text field, button, hyper-link, list, drop-down list, check-box, radio button, data grid, icon, graphical image, embedded link, etc.

In some configurations, a test subject may be part of a clinical trial. The disclosed system may be part of an initial screen at the sites administering the clinical trial. In these configurations, the clinicians and/or doctors may be screening the subject for Alzheimer's or other neurodegenerative diseases. The user may come to the testing site and interact with a computer or mobile device in an environment controlled by the clinicians or doctors in charge of the study.

In some situations, the subject may be a patient coming to a doctor for screening to determine if the subject requires further examination (e.g., MRI, PET scan, etc.). In these situations, the patient may use a laptop computer or mobile device (e.g., ipad) as the client 120 used to administer the test in the waiting room. Odors may be delivered to the patient while the patient is holding the mobile device and waiting for the doctor. In these configurations, by the time the patient sees the doctor, the doctor would already have the results during the doctor/patient interview in order to advise the patient whether they need additional care.

In some configurations, a user may self-administer the tests, for example, via a website accessible via a remote client 120, such as a user's home computer or mobile device. In these configurations, a user may purchase a card or other system for detecting the relevant odors (possibly a reversion to a scratch and sniff card model), and access a website for the test. The user may have a specific login and password to identify the user. The user's data may be correlated to the purchased card and the test may be administered online by comparing the user's answers to the correct odors on the card. This test does not constitute a medical opinion, only a means for users to generally monitor their health by receiving feedback on their olfaction.

In some configurations, the client 120 may receive input from the user, and this input may be used to run calculations for the results of the tests derived from the algorithms disclosed below. In some configurations, the input received by the client may be used to run calculations via a combination of server(s) 110 and/or client 120. For example, in the waiting room tests and tests administered online described above, the test may be displayed, and the user's responses may be received via the client 120, but the display may be generated, the user's responses received, and the calculations to determine the results run on one or more servers 110 at a location remote from the client 120. Server(s) 110 may include a computer or program that provides services to other computers, programs, or users over a computer network.

The software modules running on server(s) 110 and/or client(s) 120 may generate the display for the user, including the options presented to the user, using data stored in database 130. The software modules may also be configured to calculate the test results based on the user's input and store these results in database 130. Structurally, the database may include a collection of data, and this data may be stored for a length of time, for example, with a secure server in the cloud, providing access to the generated data as desired.

Multiple tests, as described below, may be administered via the disclosed system. These tests may incorporate working memory and episodic memory of odor percepts (referred to herein as odor memory tests or POEM tests), which would improve the sensitivity and specificity of olfaction as a biomarker of preclinical Alzheimer's disease, since performance on these tasks would be expected to reflect the integrity of both the olfactory and memory neural systems. An odor percept is the mental impression of an experienced smell.

In some configurations, all of the disclosed tests are administered in a single session. In some situations the test may take about 30 minutes (e.g., 3 tests with a 10 minute interval between each). For each test, subjects may be seated next to the olfactometer, given test instructions, and may undergo a trial run of odor presentation and response choice to acclimate to the timing and tasks of the test.

At the end of the test battery, the disclosed system software may determine whether the user has been a good or poor performer in relation to the odor memory or POEM tests. The software may make this determination via the algorithms disclosed herein, and may generate the results of the tests and the interpretation of these test results (e.g., whether or not the subject a poor POEM performer, and therefore at risk of neurodegenerative disease) in real time. The results of the tests and interpretation of the results may then be displayed as a report to the physician. The physician may then present and contextualize the result for the patient, similar to how this is currently done with radiology and LP results. In a direct consumer test, the result stated may be more general regarding olfactory function.

A working memory delay component is introduced into odor identification (referred to as odor identification, odor percept identification or OPID tests, e.g., OPID-10) and/or odor memory tests (e.g., odor memory, odor percept identification or OPID-20) by having participants answer a yes/no question between the odor delivery and prior to the presentation of odor identification choices. In the odor identification test, the yes/no question is whether the participant finds the odor to be familiar; in the odor memory test, it is whether the presented odor was included among the first set of odors.

Figure 3:
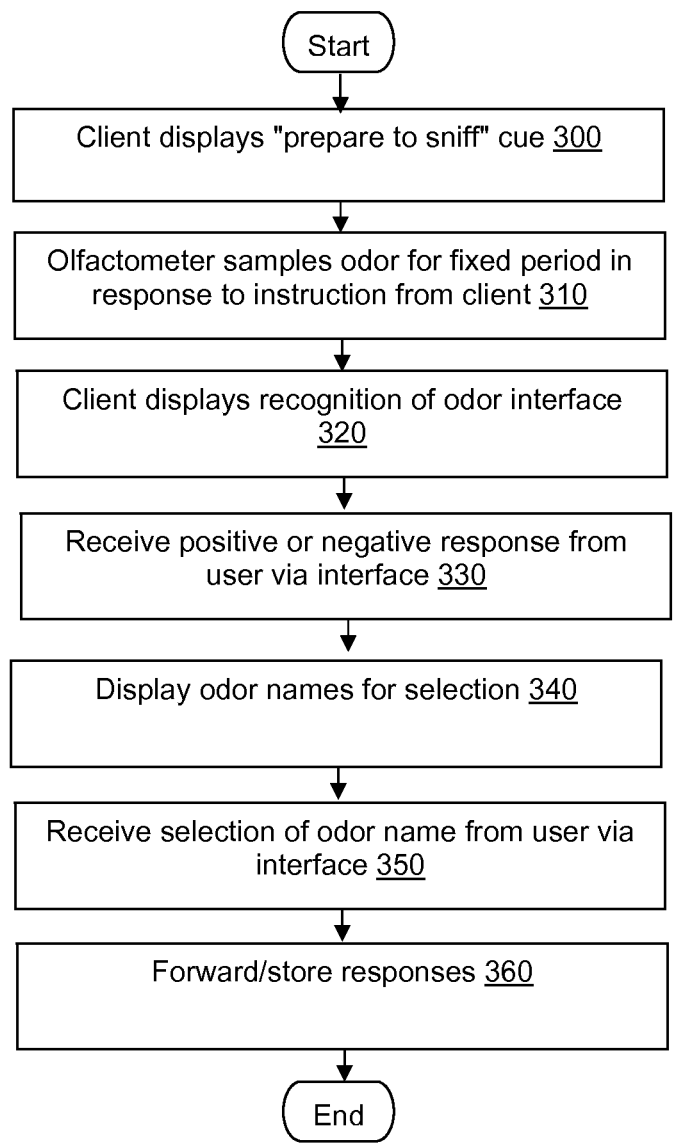
FIG. 3 illustrates a flow diagram for an odor identification test used in screening neurodegenerative diseases using an olfactometer.
Figures 4, 5:
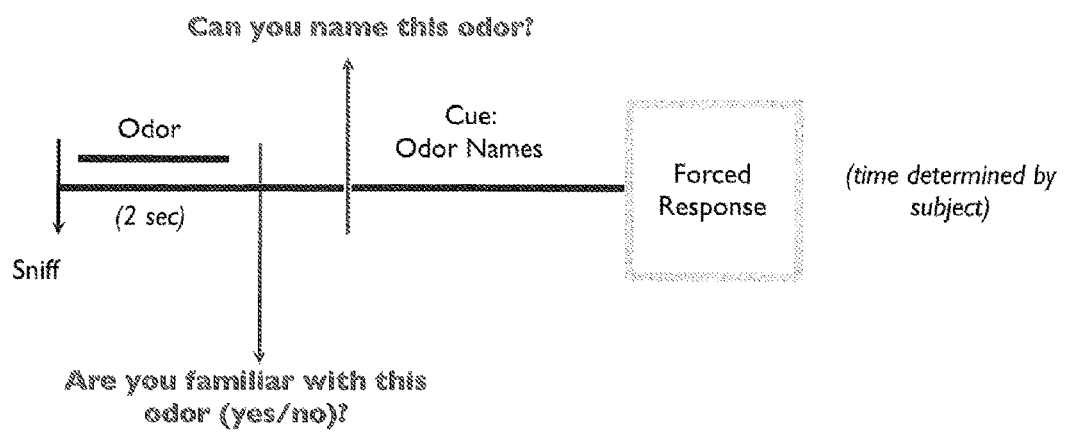
FIG. 4 illustrates a flow diagram for an odor identification test used in screening neurodegenerative diseases using an olfactometer.
FIG. 5 illustrates an example user interface for an odor identification test used in screening neurodegenerative diseases using an olfactometer.
Figure 6:
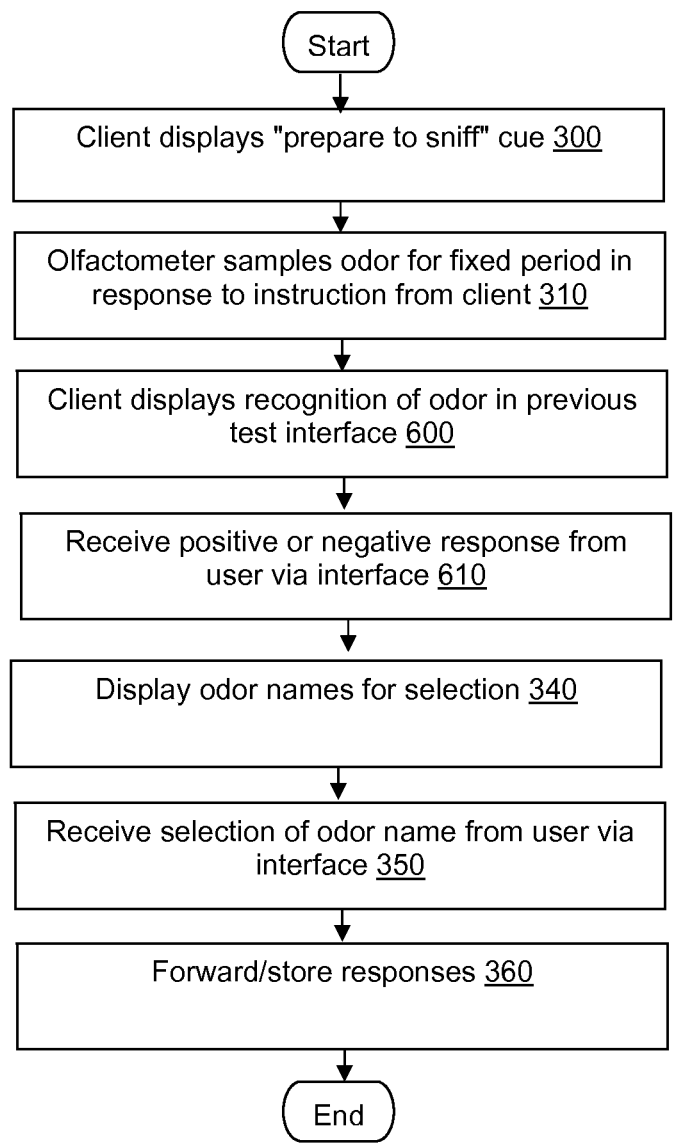
FIG. 6 illustrates a flow diagram for an odor memory test used in screening neurodegenerative diseases using an olfactometer.

The first test, the odor identification test, may include the test illustrated in FIGS. 3-5. In traditional scratch-and-sniff tests, the response choices are viewed by the participant before sampling the test odor. In disclosed odor memory tests, the participant has no visual or semantic information to contextualize the odor that s/he is sniffing.

The odor identification test employs a plurality of odors (e.g., the first ten odors listed above) found to be predictive for conversion from Mild Cognitive Impairment to a neurodegenerative disease, such as Alzheimer's disease This test is referred to as an odor percept identification test because it requires the subject to identify an odor based on the subject's odor percept, or what the subject remembers, and by so doing, builds the subject's working memory into that test.

In this test, the subject may be cued to prepare to sniff (Step 300). In some configurations, server(s) 110 and/or client 120 may be configured to generate and display a user interface such as that seen in FIG. 5 to the subject, cuing the subject to prepare to sniff and sample the delivery of the odor for a fixed period (e.g., two seconds) (Step 310).

This approach breaks from traditional paradigms because the subject is given no expectation of what odor to expect. In other words, rather than presenting the subject a list of odors that the subject may smell, the disclosed system simply tells the user to prepare to sniff with no hints as to the origin of the odor.

The olfactometer 150 may then receive a command from the client 120 to present the odor to the subject, and may execute this command by presenting one of odors to the subject (Step 310) for a fixed period (e.g., two seconds in FIG. 4). In some configurations, each response choice and reaction time may be recorded by the software program that triggers the olfactometer 140 and may be used to weight responses.

At the end of the specified time period, and immediately following odor presentation, the software modules on server(s) 110 and/or client 120 may generate a display as seen in FIG. 5, asking the user, via a yes/no menu, whether the subject is familiar with the odor (Step 320). In some configurations, the display may indicate that familiarity with the odor percept does not require a semantic label.

Client 120 may receive the odor identification response (e.g., yes or no) from the subject (Step 330). This response may be forwarded to and utilized by the algorithms disclosed herein for calculating and displaying the results of the test, and/or may be stored within the database 130, possibly as one or more data records associated with the tested subject. In response to the receipt of the subject selecting yes or no, the software modules may generate a display as seen in FIG. 5, asking the user if they can name the odor (Step 340). The subject may then be presented with a plurality of odor names (a, b, c and d in FIG. 5) and asked to choose which odor name is associated with their memory of the odor percept experienced at the start of the trial. In some configurations, a graphic may accompany the choices (not shown in FIG. 5). Client 120 may receive the odor identification response from the subject (Step 350). This response may be analyzed and scored, forwarded to the algorithms disclosed herein for calculating and displaying the results of the test, and/or may be stored within the database 130, possibly as a data record associated with the tested subject (Step 360).

An odor awareness scale test may provide a measure of how attentive subjects are to their olfactory sense and how influenced they are behaviorally and emotionally by their olfactory perceptions (e.g., queries regarding odor awareness in their environment). This test includes a survey that the subject fills out between a test and the next test. In some configurations, this test does not contribute at all to the variants being observed in the other tests, but serves as a consistent delay between the tests.

Figures 7, 8:
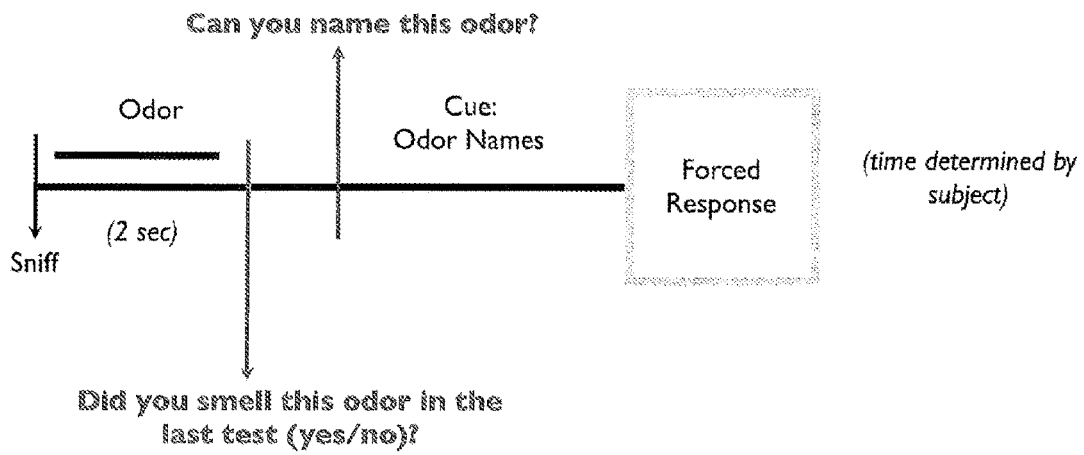
FIG. 7 illustrates a flow diagram for an odor memory test used in screening neurodegenerative diseases using an olfactometer.
FIG. 8 illustrates an example user interface for an odor memory test used in screening neurodegenerative diseases using an olfactometer.
Figure 9:
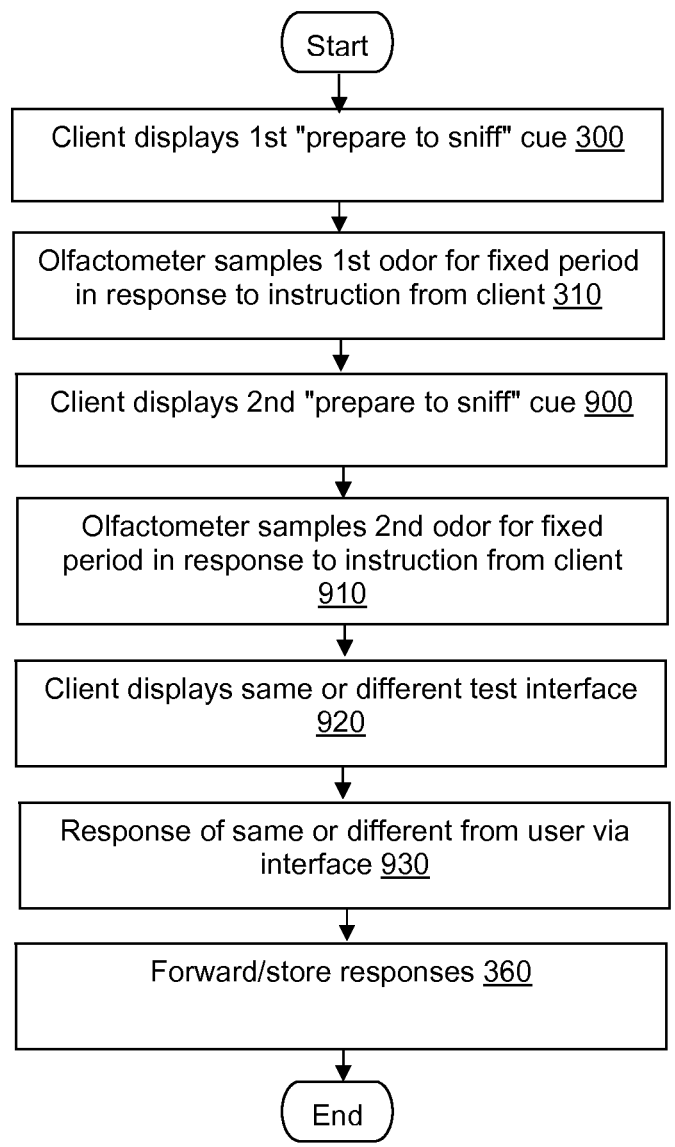
FIG. 9 illustrates a flow diagram for an odor discrimination test used in screening neurodegenerative diseases using an olfactometer.

Additionally or alternatively, a multiple-item test (e.g., 20 items including the odors listed above) may be performed that includes two components, seen in FIG. 7: an odor memory test and an odor identification test. The protocol is similar to the original odor identification test except the question following the presentation of the odor is "Did you smell this odor in the previous test?"

In this test, the subject may be cued via the display to prepare to sniff (again, this may be optionally done with no expectation of what the subject is going to smell, Step 300), and the olfactometer presents the odor(s) to the subject for a fixed period, using techniques analogous to those previously disclosed, with 10 of the odors having been presented in the OPID-10 test and 10 of the odors being new to the POEM/OPID-20 test this testing session (i.e.,).

At the end of the specified time period, and immediately following odor presentation, the software modules running on the server(s) 110 and/or client(s) 120 may generate a display as seen in FIG. 8, asking the user, via a yes/no menu, whether the subject smelled the odor in the previous test (Step 600). Thus, the odor memory test measures the subject's ability to remember previously presented odors after a delay of a fixed period (e.g., 10 minutes) with no clues, and further measures how accurate the subject was in identifying the odor. Put another way, subjects may be asked if the odor presented was new or had been presented in the earlier odor percept identification test. In some configurations, the instruction phase of the test may include an explicit indication that the new/old designation refers to the current testing session and not to a broader lifetime exposure.

Following this measure of episodic or autobiographical odor memory (Step 600), subjects may be presented with a plurality of odor names, and asked to choose which name associated with their memory of the odor percept they experienced at the start of the trial (Step 340). In other words, in response to the receipt of the subject selecting yes or no, server(s) 110 or client 120 may generate a display as seen in FIG. 8, asking the user if they can name the odor (Step 340). The subject may then be presented with a plurality of odor names (a, b, c and d in FIG. 8) and asked to choose which odor name is associated with their memory of the odor percept experienced at the start of the trial. In some configurations, a graphic may accompany the choices (not shown in FIG. 8). Client 120 may receive the odor memory/identification response (e.g., yes or no) from the subject, as well as the odor name associated with their memory/identification of the odor percept experienced. These responses may be analyzed and scored, forwarded to the algorithms disclosed herein for calculating and displaying the results of the test, and/or may be stored within the database 130, possibly as a data record associated with the tested subject (Step 360).

Figures 10, 11:
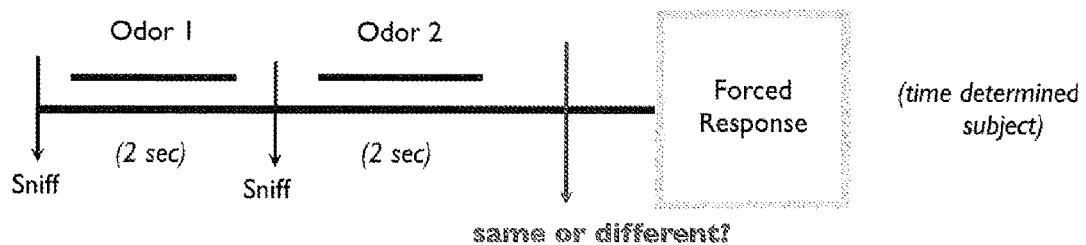
FIG. 10 illustrates a flow diagram for an odor discrimination test used in screening neurodegenerative diseases using an olfactometer.
FIG. 11 illustrates an example user interface for an odor discrimination test used in screening neurodegenerative diseases using an olfactometer.

Additionally or alternatively, an odor discrimination test (referred to as an odor discrimination or OD test) may be performed, seen in FIG. 10, where subjects are presented two odors consecutively for a fixed time period (e.g., two seconds each) and asked if the odors were the same or different.

In this test, the subject may be cued via the display to prepare to sniff (Step 300, again, with no expectation of what the subject is going to smell), and the olfactometer presents the odor(s) to the subject for a fixed period, using techniques analogous to those previously disclosed (Step 310). At the end of the specified time period (e.g., two seconds in FIG. 10), the olfactometer presents an odor to the subject for the same fixed period, one after the other, using techniques analogous to those previously disclosed.

In other words, during the odor discrimination test, the subject may be cued on each trial to prepare to sniff bilaterally and sample the delivery of multiple odors presented consecutively, each for a fixed time period (Steps 300-310 and 900-910). Subjects may then be asked if the odors presented were the same or different (Step 920). In some exemplary configurations, half of the trials are the same, and the odors included are a predetermined selection of the odors listed above. The odors may be a subset of previously exposed odors.

After the odors have been presented to the user, the software modules executed by the server(s) 110 and/or client 120 may generate a display as seen in FIG. 11, asking the user, via a menu, whether the consecutively presented smells were the same or different.

Client 120 may receive the odor discrimination response (e.g., same or different) from the subject (Step 930). This response may be analyzed and scored, forwarded to the algorithms disclosed herein for calculating and displaying the results of the test, and/or may be stored within the database, possibly as one or more data records associated with the subject (Step 360).

A combination of software instructions executed by the software modules running on server(s) 110 or client 120 may receive the user input from each and all of the tests and may compare the subject's responses against the correct answers to responses to the prompts (possibly stored in database 130) received by the user in order to determine if the received answers match the correct answers. The software modules may then run calculations to analyze the subject's answers and generate a score including the number of correct answers for all or each of the odor identification, odor memory and/or odor discrimination tests.

After generating these scores, the odor discrimination and the identification tests may be analyzed separately in order to generate a plurality of predicted odor memory scores and confidence interval thresholds (e.g., a 50% confidence interval) for the subject, which may be used in part to determine whether the subject is a poor odor memory performer and therefore susceptible to neurodegenerative diseases.

The subject's predicted odor memory scores may be based in part on a relationship between the odor identification score and the first predicted odor memory score, which may be generated from the subject's odor identification score, based on an aggregation, stored in database 130, of performance and results data from previous studies and/or test subjects. This relationship between the odor identification score and the first predicted odor memory score may be linear. The aggregation of performance and results data in database 130 may further be used to generate a second and separate predicted odor memory score, which may be based on a relationship of the subject's odor discrimination score and the aggregation of data of performance and results of previous studies and/or test subjects. This relationship between the subject's odor discrimination score and the aggregation of data of performance and results of previous studies and/or test subjects may be linear.

A final step in the analysis may include comparing the actual memory score with predicted memory score using the lower 50% confidence interval as the threshold. Subjects whose observed memory score is less than this threshold for both tests may be deemed poor POEM performers. This may convey an increased risk of neurodegeneration and an increased risk to develop the symptoms of neurodegenerative disease.

The aggregation of performance and results data in database 130 may be based on the results of research studies and/or additional user tests used to determine the first and second predicted odor memory scores and the confidence interval thresholds of previous subjects or studies. In a non-limiting example of such a study, Massachusetts General Hospital (MGH) Department of Neurology in Boston performed a study relating the ability to identify and recall odor precepts to biomarkers of Alzheimer's disease. This study targeted identification of biomarkers for the pre-clinical, the pre-symptomatic, stage of Alzheimer's disease.

For some time, pathological studies and other reports determined olfactory changes in the late stages of dementia as well as in a transition state where patients have symptoms that haven't reached the criteria for dementia. As noted above, the predominant current test in the field is the scratch and sniff smell identification test.

The goal of the MGH study was to consider a non-invasive and inexpensive technique (relative to PET imaging, MRI, and lumbar puncture) to identify possible instances of dementia earlier into the pre-symptomatic phase. In the study, selective impairment of episodic memory of odor precepts, relative to identification and discrimination of odor precepts, were associated with biomarkers of Alzheimer's disease in a well-characterized pre-mild cognitive impairment population. The affordable, non-invasive olfactory tests described above were used to potentially identify clinically normal individuals at elevated risk of cognitive decline.

The study detected and followed individuals at risk for neurodegenerative disease by incorporating a memory component into the test as demonstrated in the odor identification, odor memory and odor discrimination tests, the odor memory component being more specific to Alzheimer's disease at a preclinical stage than olfactory deficit tests, such as those used for Parkinson's disease, for example.

Data from the study determined that olfactory outcomes in participants who were clinically normal, but that performed poorly on the POEM test relative to performance on identification task, OPID-20 and the discrimination task, OD, were associated with worsening stages of Alzheimer's disease and all accepted risk factors for the development of Alzheimer's disease. Specifically, these participants were associated with significantly worse trajectory of a cognitive score (described in more detail below), and an increase in APOE ε4 gene (the gene allele most significantly associated with sporadic Alzheimer's disease).

This data also determined sensitivity to neurodegeneration, which can occur very early in the preclinical period. The regions of the brain that process olfactory input, including the entorhinal cortex (a marker of neurodegeneration in a relevant brain region for very early Alzheimer's disease), and the olfactory bulb, are vulnerable to Alzheimer's disease pathology, even in asymptomatic individuals. Impaired smell identification is a consistent finding in patients in the dementia and prodromal stages of Alzheimer's disease, and has recently been reported in the preclinical stages of Alzheimer's disease as well.

The study included 183 participants, to which the OPID-10, OPID-20/POEM and OD tests were administered, and follow up was performed on the subjects on an annual basis. The participants ranged from cognitively normal (CN) to demented (AD). The participants were subdivided into subgroups including: CN, meaning that the subgroup had no cognitive symptoms and no problems on neuro-psychological tests on an annual basis; subjective cognitive concerns, including a subgroup who reported cognitive concerns (i.e., may have symptoms) but had normal cognitive testing; Mild Cognitive Impairment (MCI), including participants diagnosed with amnestic or non-amnestic mild cognitive impairment, but not dementia; and AD dementia, including subjects with possible or probable Alzheimer's disease.

The data for all subjects was analyzed, and a linear mixed modeling of longitudinal cognitive scores was performed, separating the demented patients from the earlier stages of dementia. Accuracy of identification and episodic memory of odor percepts differed significantly across diagnosis and age, with progressively worse performance across degrees of impairment.

In the study, subjects without symptoms who completed the tests where discovered who scored normally on the OPID-20 test and the OD test, but their POEM score was worse than would have been predicted based on their scores on the other two tests (referred to herein as "poor POEM performers"). It should be noted that poor POEM performers are not limited to those who score normally on the OD and OPID-20 tests. It is possible to score poor on the OD or the OPID-20 tests and also score poorly on the POEM test, thereby achieving poor POEM performer status. This was significant, in that, within this example study, the poor POEM performers within the "normal" group had a predicted POEM score, based on their OPID-20 and OD tests, below a 50% confidence interval, and were therefore more susceptible to Alzheimer's disease. The study determined that poor POEM performers in the CN or SCC subgroups were enriched with three well accepted risk factors and biomarkers for neurodegeneration and/or Alzheimer's, including evidence of enrichment (i.e., higher frequencies) in the APOE e4 risk allele, reduction (i.e., thinning) of entorhinal cortical thickness, and greater longitudinal decline in Logical Memory scores (i.e., worse cognitive trajectory relative to non-poor-POEM performers, described below). Thus, logistic regression modeling revealed significant differences in POEM test performance between Alzheimer's disease participants and those in the CN and SCC groups.

Modeling the proportion of correct responses by logistic regression revealed significant main effects of diagnosis ($\chi^2(3)=13.28$, $p<0.0001$) and age ($\chi^2(1)=6.01$, $p=0.01$), when controlling for covariate effects. Relative to Alzheimer's disease participants, the log odds of correctly distinguishing previously presented odors was 54.3% higher for the CN group ($p=0.003$) and 44.9% higher for the SCC group ($p=0.016$). For a given diagnosis, gender and education level, the log odds of correct episodic recall decreased by 0.011 ($p=0.014$) for every year the participant aged. In secondary analyses, accounting for diagnosis, age, education, and gender effects, performance on the POEM test was not significantly associated with other examined biomarkers, including neuropsychological memory tests.

Logistic regression modeling of the OD outcome showed significant differences in performance between the CN and AD diagnoses. Modeling the proportion of correct responses revealed significant main effects of diagnosis ($p=0.01$) and age ($p<0.0001$), when controlling for covariate effects. In secondary analyses, controlling for diagnosis and covariate effects, the study found that worse OD performance was significantly associated with a higher Trails B score ($p<0.0001$).

The episodic recognition of odors as previously (or not previously) presented in the OPID-20 is a complex task that relies on both the ability to discriminate and identify odor percepts. Consistent with this, performance on the POEM and the OD and OPID-20 tests were substantially correlated across the study's sample. The study hypothesized that individuals who had pathophysiological changes in the olfactory/entorhinal cortical neural systems would perform less well on the memory component relative to the identification and discrimination tasks, even early on in disease. In order to identify individuals with specific deficits in episodic memory of odor percepts, the study developed prediction models for POEM scores as a function of the OPID-20 and the OD tests. CN and SCC participants with POEM scores less than the lower bounds of the 50% confidence interval of the predicted scores from each were identified as poor POEM performers (PPPs, n=23; 21%) and the remainder were identified as good POEM performers (n=88). This 50% threshold was based on initial observations that POEM index scores of the lowest quartile of CN participants approximated the range of scores of the AD participants (whose performance was no better than chance). Good performers and poor performers on the POEM test did not differ from one another on their performance of the discrimination (78.0±1.4% correct vs. 78.3%, p=0.9) or on other demographic variables, including the UPDRS test related to Parkinson symptoms. However, PPPs did perform worse on the identification tasks (OPID-20: 76.4% correct vs. 68.8%, p=0.04)

Consistent with above-described systems and methods, the sensitivity and specificity of the POEM test (90% and 78%, respectively) exceeded the OPID-20 (80% and 69%, respectively) and OD (70% and 66%, respectively) for the diagnosis of Alzheimer's disease. Thus, the study identified people without memory symptoms with a poor trajectory of the subjects' cognitive function.

Notably, the trajectory of the subjects' cognitive function in the poor POEM performer group was significantly different than the good POEM performer group, who performed in a proportional manner. In this study, for the first 8 years, the good POEM performers' scores improved year over year, while the poor POEM performers' scores stayed flat or even declined (i.e., even though they were still in the "normal" range, their trajectory either remained flat or declined).

Figure 12:
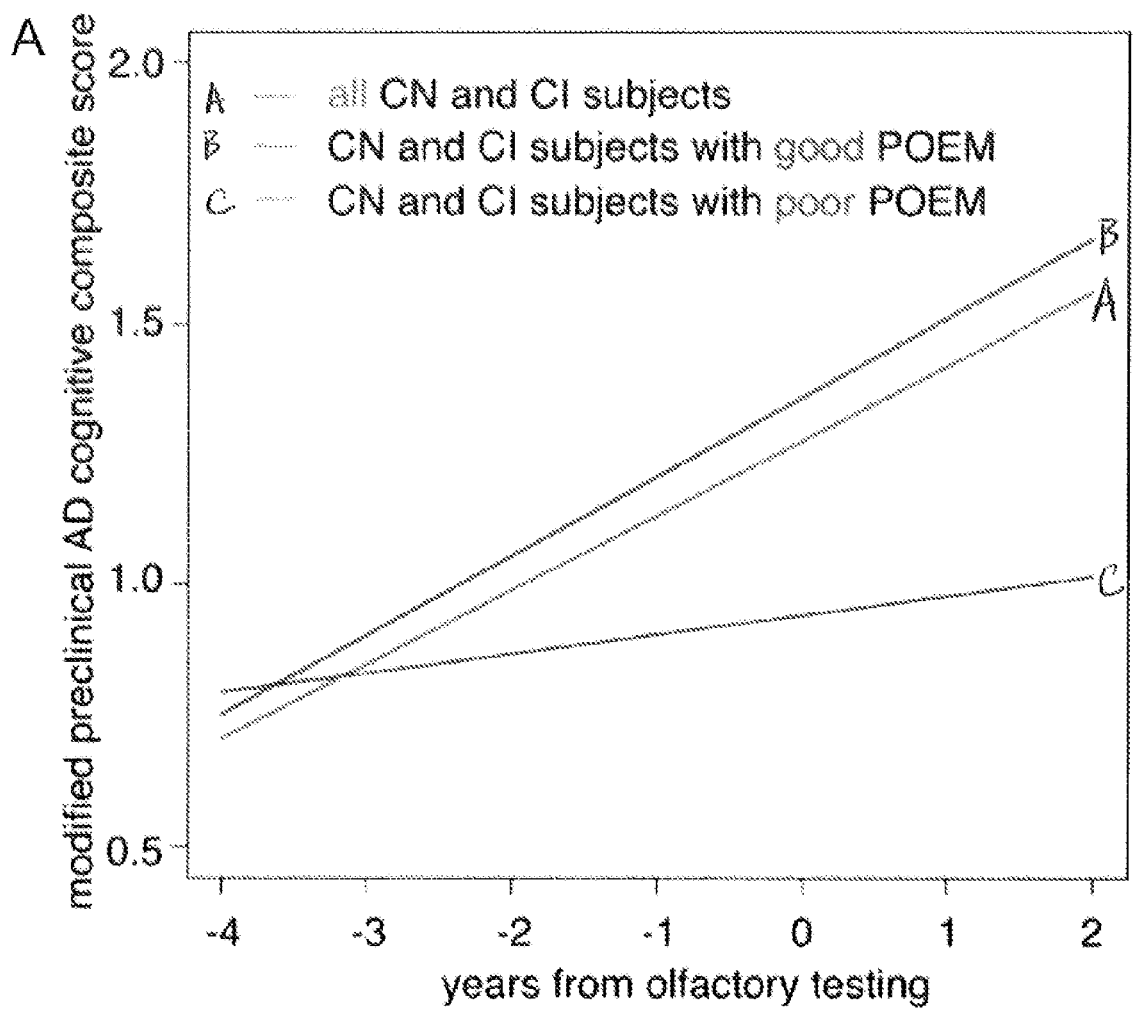
FIG. 12 illustrates an example result of a study for screening neurodegenerative diseases using an olfactometer.

FIG. 12 demonstrates a non-limiting example of Modified Preclinical Alzheimer's Cognitive Composite scores calculated for CN/CI subjects that underwent olfactory testing once and had over 6 years of annual neuropsychological testing. The linear mixed model reveals a significant association with age and visit number without any interaction effects. The model plotted for all CN/CI subjects that underwent olfactory testing. and the subset of those CN/CI subjects with commensurate POEM performance (good POEM performers) are overlapping.

However, the cognitive trajectory of the subset of CN/CI subjects with POEM performance below the 50% confidence interval after correcting for OPID-20 and OD scores (poor POEM performers) over the same time span is significantly worse than that of the overall CN/CI group and that of the CN/CI good POEM performers.

Figure 13:
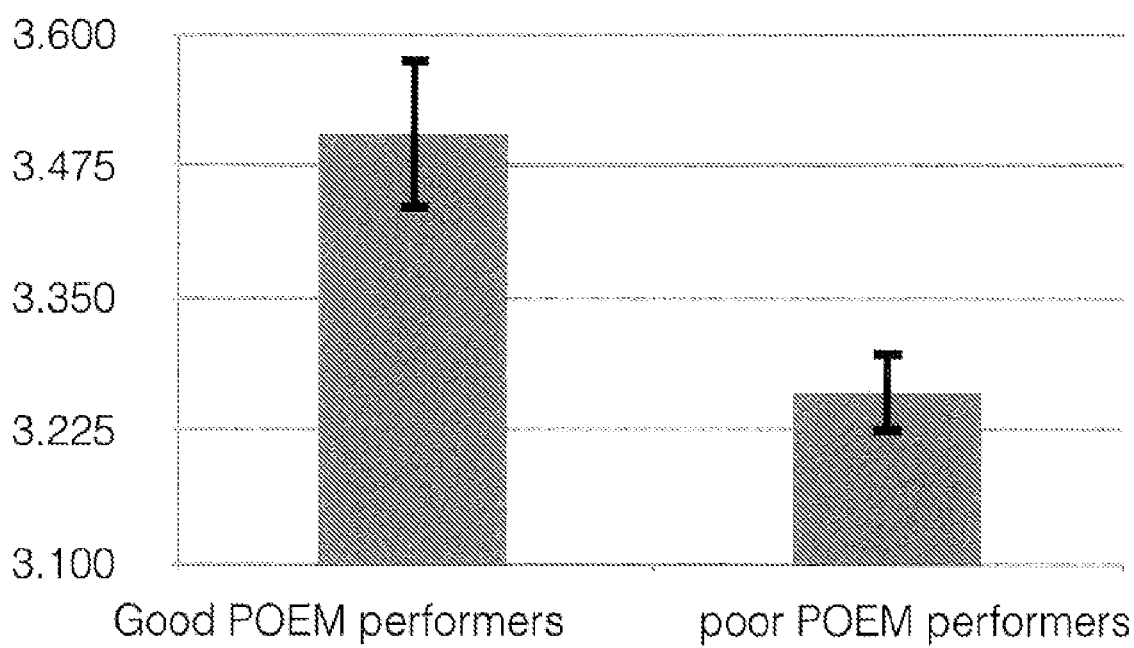
FIG. 13 illustrates an example result of a study for screening neurodegenerative diseases using an olfactometer.

FIG. 13. demonstrates that, in the subset of olfactory tested CN/CI subjects who underwent volumetric MRI, average entorhinal thickness of non-poor POEM performers was significantly greater than the poor POEM performers.

This separation of patients based on the data was developed via the introduction of the concept of poor POEM performers (subjects receiving a POEM score falling below a 50% confidence interval of their predicted performance based on their performance in the OPID-20 and OD tests), may therefore be used to identify those subjects who may be at risk for Alzheimer's disease.

Figure 14:
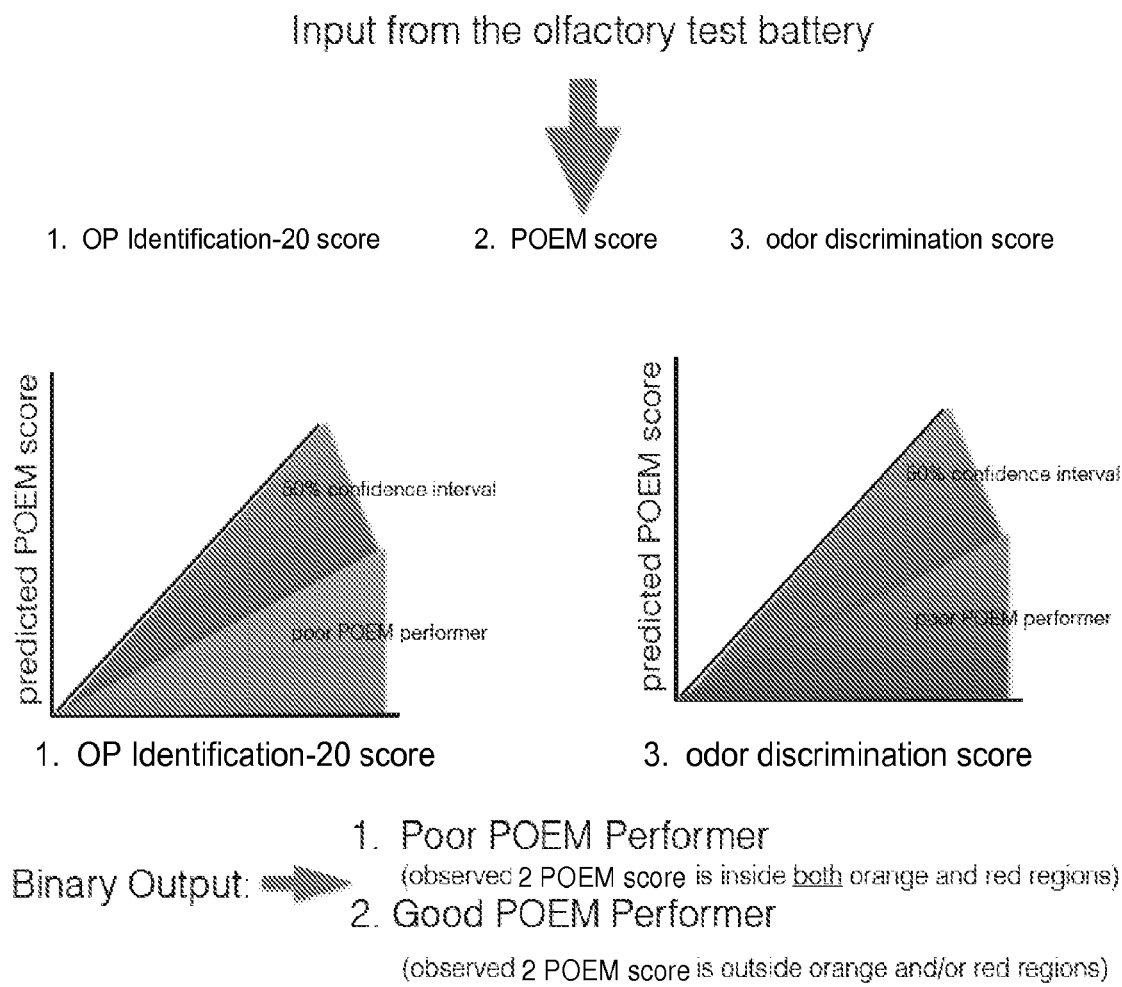
FIG. 14 illustrates a flow diagram for screening neurodegenerative diseases using an olfactometer.

The example study explained above should in no way limit the scope of the claimed invention. As seen in FIG. 14, described in more detail below, data within a database (e.g., an aggregation of research data from a specific research study as above, data entered by a data or system administrator, etc.), may be used to calculate the predicted odor memory score for the odor memory/identification or odor discrimination tests and/or confidence interval threshold for each when identifying a subject as a good or poor odor memory performer.

This collected data may be imported and stored in a database, such as a customized MySQL database. Calculations of episodic odor memory index, and percent accuracy in the odor discrimination and odor identification tests may be automatically calculated by the software modules executed by server(s) 110 or client 120 in conjunction with exporting data out of the database 130 for analysis.

Put another way, as seen in FIG. 14, the software modules may be configured to query the database for data including previously-entered performance data (e.g., studies, test results) relevant to odor memory/identification test results (e.g., from previous studies and/or entered by a data or system administrator). Using this previously-entered performance data returned from the database query, the software modules may calculate a predicted odor memory score (a prediction of an expected memory score) based on a linear relationship between the subject's odor memory/identification score and the previously-entered performance data in the database 130. The predicted odor memory score based on the linear relationship between the subject's odor memory/identification score and the previously-entered performance data in the database may include or be used to calculate a confidence interval threshold for the predicted odor memory score, based on a variance/scattering of the dataset. Both calculations may be determined using algorithms analogous to those used in the MGH research study.

Similarly, the software modules may be configured to query the database for data including previously-entered performance data relevant to odor discrimination test results. Using this previously-entered performance data returned from the database query, the software modules may calculate a predicted odor memory score based on a linear relationship between the subject's odor discrimination score and the previously-entered performance data in the database. The predicted odor memory score based on the linear relationship between the subject's odor discrimination score and the previously-entered performance data in the database may include or be used to calculate a confidence interval threshold for the predicted odor memory score, based on a variance/scattering of the dataset. Both calculations may be determined using algorithms analogous to those used in the MGH research study.

The software modules may use the predicted odor memory score for the odor memory/identification and odor discrimination tests to calculate whether the user has a selective odor memory deficit. As seen in FIG. 14, the algorithm to determine whether the user is a poor POEM performer and generate the appropriate results report may include the software modules running on server(s) 110 and/or client 120 receiving input from the olfactory battery test. In some configurations, this input includes the test scores for the POEM/OPID-20 and OD scores.

The predicted odor memory score for both the odor memory/identification test and the odor discrimination tests may be generated as seen in FIG. 14. The software combination may determine whether the subject's odor memory/ identification score was below the confidence interval threshold of the predicted odor memory score for the odor memory/identification test, and whether the odor discrimination score was below the confidence interval threshold of the predicted odor identification score for the odor discrimination test.

If the software algorithm determines that the subject's odor memory/identification score or the subject's odor discrimination scores are greater than the confidence interval threshold of the respective predicted odor memory scores, or in other words, falls within the confidence interval threshold, the software may designate the subject as a good POEM performer. However, if the software algorithm determines that the subject's odor memory/identification score and the subject's odor discrimination scores are less than the confidence interval threshold for the respective predicted odor memory scores, or in other words, falls outside the confidence interval threshold, the software may designate the subject as a poor POEM performer. This is an identifying feature that suggests that the subject is at risk for Alzheimer's or other neurodegenerative diseases, and the software may be configured to generate and display a report to the subject accordingly.

The disclosed system may be flexible enough to modify or refine the tests or the described environment. For example, if the sensitivity or specificity of the tests needed to be modified, the disclosed system may provide means to modify the disclosed tests.

In addition to collecting answers from the subject, additional information may be collected. For example, in addition to determining whether or not the subject answered the question correctly, the system may be configured to determine the amount of time it takes the subject to respond to the answer and/or select a response. As seen in FIGS. 4, 7 and 10, time may be determined by subject, thus, the system may record a subject's response time to determine how long it takes them to make a decision.

In some configurations, instead of just showing 4 possible answers, the software may be configured to initially show a greater selection of potential answers, then reduce the number of responses available (e.g., the displayed interface may initially have 10 possible answers, then for each of the delivered odors, may reduce the number of options available to the subject.

Depending on the options available to the subject, the test could be fine tuned so that the responses could become increasingly or less difficult depending on how close the choices are to the actual odor. For example, if the odor is a fruit odor, and there are 4 different fruits presented to the subject, the test would be more difficult, as opposed to presenting 1 fruit and 3 things different than fruit (e.g., leather, garlic, dirt). The difficulty of the test may help to fine tune the final determination of the user's poor or good POEM performance.

In some configurations, biographical information may be used to correlate scores more accurately. Demographics may be important, and demographically appropriate odors may be used to ensure the subject should be familiar with the odors presented, particularly for a clinical or consumer test.

Likewise, in some configurations, medical information may be used to correlate scores more accurately, such as medical conditions that may invalidate certain scents (e.g., asking about smoking, an active smoker or not, nasal polyps, surgery for deviated septum or plastic surgery, etc.) These considerations may need to be taken into account when determining the subject's score.

The steps included in the configurations illustrated and described in relation to FIGS. 1-6 are not limited to the configuration shown and may be combined in several different orders and modified within multiple other configurations. Although disclosed in specific combinations within these figures, the steps disclosed may be independent, arranged and combined in any order and/or dependent on any other steps or combinations of steps.

Other embodiments and uses of the above inventions will be apparent to those having ordinary skill in the art upon consideration of the specification and practice of the invention disclosed herein. The specification and examples given should be considered exemplary only, and it is contemplated that the appended claims will cover any other such embodiments or modifications as fall within the true scope of the invention.

The Abstract accompanying this specification is provided to enable the United States Patent and Trademark Office and the public generally to determine quickly from a cursory inspection the nature and gist of the technical disclosure and in no way intended for defining, determining, or limiting the present invention or any of its embodiments.

The invention claimed is:

1. A system, comprising:
   an olfactometer configured to deliver an odor from among a plurality of odors; and
   a computing device comprising instructions that, when executed by a processor running on the computing device, cause the computing device to:
   generate a user interface to be displayed on the computing device;
   receive, via the user interface, a user input for each of an odor memory test, two odor identification tests, and an odor discrimination test;
   calculate, based on a plurality of correct answers queried from a database, a score for each of the odor memory test, the odor identification tests and the odor discrimination test;
   calculate, from a relationship between the score for the odor memory test and a plurality of previously-entered performance data queried from the database, a first confidence interval threshold for a first predicted odor memory score;
   calculate, from a relationship between the score for the odor discrimination test and the plurality of previously-entered performance data, a second confidence interval threshold for a second predicted odor memory score based on at least one of the odor identification tests;
   determine whether the score for the odor memory test is greater than the first confidence interval threshold and the score for the odor discrimination test is greater than the second confidence interval threshold; and
   responsive to a determination that the score for the odor memory test is not greater than the first confidence interval threshold and the score for the odor discrimination test is not greater than the second confidence interval threshold, generate a report, to be displayed by the computing device, identifying a user as high risk for a neurodegenerative disease.

2. The system of claim 1, wherein the instructions include steps for administering at least one of the odor identification tests that cause the computing device to:
   transmit an instruction to the olfactometer to deliver the odor;
   generate the user interface comprising:
   a cue that the odor will be delivered;
   an odor recognition user interface component;
   an odor selection user interface component comprising a plurality of odor selections;

receive from the user, via the at least one user interface:
a positive or negative response, via the odor recognition user interface component, indicating whether the user recognizes the odor;
a selection, via the odor selection user interface component;
query the database to identify a correct response for the selection;
calculate the score for at least one of the odor identification tests, wherein, if a correct response matches the selection, the score is increased, and if the correct response does not match the selection, the score is decreased.

3. The system of claim 1, wherein the instructions include steps for administering the odor memory test that cause the computing device to:
transmit an instruction to the olfactometer to deliver the odor;
generate the user interface comprising:
a cue that the odor will be delivered;
a previous odor recognition user interface component;
an odor selection user interface component comprising a plurality of odor selections;
receive from the user, via the at least one user interface:
a positive or negative response, via the previous odor recognition user interface component, indicating whether the user recognizes the odor from the first odor delivered;
a selection, via the odor selection user interface component;
query the database to identify a correct response for the selection;
calculate the score for the odor memory test, wherein, if a correct response matches the selection, the score is increased, and if the correct response does not match the selection, the score is decreased.

4. The system of claim 1, wherein the instructions include steps for administering the odor discrimination test that cause the computing device to:
transmit an instruction to the olfactometer to deliver a first odor and a second odor from among the plurality of odors;
generate the at least one user interface comprising:
a cue that the first odor will be delivered;
a cue that the second odor will be delivered;
an odor discrimination user interface component;
receive from the user, via the at least one user interface:
a selection, via the odor discrimination user interface component, indicating whether the first odor and the second odor were the same or different;
query the database to identify a correct response for the selection;
calculate the odor discrimination score, wherein, if the correct response matches the selection, the score is increased, and if the correct response does not match the selection, the score is decreased.

5. The system of claim 1, wherein, prior to the olfactometer delivering the odor, the user interface comprises no indication of an expected odor.

6. The system of claim 1, wherein the computing device calibrates the first predicted odor memory score and the second predicted odor memory score according to the score for at least one of the odor identification tests and the odor discrimination test.

7. A method, comprising the steps of:
requesting, by a computing device communicatively coupled to a network delivery of an odor, from among a plurality of odors, from an olfactometer;
generating, by the computing device, a user interface to be displayed on the computing device;
receiving, by the computing device via the user interface, a user input for each of an odor memory test, two odor identification tests, and an odor discrimination test;
calculating, by the computing device, based on a plurality of correct answers queried from a database, a score for each of the odor memory test and the odor discrimination test;
calculating, by the computing device, from a relationship between the score for the odor memory test and a plurality of previously-entered performance data queried from the database, a first confidence interval threshold for a first predicted odor memory score;
calculating, by the computing device, from a relationship between the score for the odor discrimination test and the plurality of previously-entered performance data, a second confidence interval threshold for a second predicted odor memory score;
determining, by the computing device, whether the score for the odor memory test is greater than the first confidence interval threshold derived from at least one of the odor identification tests, and the score for the odor memory test is greater than the second confidence interval threshold derived from the odor discrimination test; and
responsive to a determination that the score for the odor memory test is not greater than the first confidence interval threshold and the score for the odor discrimination test is not greater than the second confidence interval threshold, generating, by the the computing device, a report, to be displayed by computing device, identifying a user as high risk for a neurodegenerative disease.

8. The method of claim 7, further comprising the steps of:
transmitting, by the computing device, an instruction to the olfactometer to deliver the odor;
generating, by the computing device, the user interface comprising:
a cue that the odor will be delivered;
an odor recognition user interface component;
an odor selection user interface component comprising a plurality of odor selections;
receiving from the user, by the computing device, via the at least one user interface:
a positive or negative response, via the odor recognition user interface component, indicating whether the user recognizes the odor;
a selection, via the odor selection user interface component;
querying the database, by the computing device, to identify a correct response for the selection;
calculating, by the computing device, the score for at least one of the odor identification tests, wherein, if a correct response matches the selection, the score is increased, and if the correct response does not match the selection, the score is decreased.

9. The method of claim 7, wherein the odor memory test further comprises the steps of:
transmitting, by the computing device, an instruction to the olfactometer to deliver the odor;
generating, by the computing device, the user interface comprising:
a cue that the odor will be delivered;
a previous odor recognition user interface component;
an odor selection user interface component comprising a plurality of odor selections;

receiving from the user, by the computing device, via the at least one user interface:
  a positive or negative response, via the previous odor recognition user interface component, indicating whether the user recognizes the odor from the first odor delivered;
  a selection, via the odor selection user interface component;
querying the database, by the computing device, to identify a correct response for the selection;
calculating, by the computing device, the score for the odor memory test, wherein, if a correct response matches the selection, the score is increased, and if the correct response does not match the selection, the score is decreased.

10. The method of claim 7, wherein the odor discrimination test further comprises the steps of:
  transmitting, by the computing device, an instruction to the olfactometer to deliver a first odor and a second odor from among the plurality of odors;
  generating, by the computing device, the at least one user interface comprising:
    a cue that the first odor will be delivered;
    a cue that the second odor will be delivered;
    an odor discrimination user interface component;
  receiving from the user, by the computing device, via the at least one user interface:
    a selection, via the odor discrimination user interface component, indicating whether the first odor and the second odor were the same or different;
  querying the database, by the computing device, to identify a correct response for the selection;
  calculating, by the computing device, the odor discrimination score, wherein, if the correct response matches the selection, the score is increased, and if the correct response does not match the selection, the score is decreased.

11. The method of claim 7, wherein, prior to the olfactometer delivering the odor, the user interface comprises no indication of an expected odor.

12. The method of claim 7, wherein the computing device calibrates the first predicted odor memory score and the second predicted odor memory score according to the score for at least one of the odor identification tests and the odor discrimination test, respectively.

13. The method of claim 7, further comprising the steps of:
  receiving, via the user interface, an instruction for the user to release an odor via a separate odor delivery device not controlled electronically by the user interface;
  subsequent to the release of the odor, receiving, from the user via the user interface, a response; and
  store the response by the user.

14. A non-transitory computer-readable storage media storing instructions that, when executed by at least one computing device, cause the at least one computing device to:
  request delivery of an odor, from among a plurality of odors, from an olfactometer;
  generate a user interface to be displayed on the at least one computing device;
  receive, via the user interface, a user input for each of an odor memory test and an odor discrimination test;
  calculate, based on a plurality of correct answers queried from a database, a score for each of the odor memory test and the odor discrimination test;
  calculate, from a relationship between the score for the odor memory test and a plurality of previously-entered performance data queried from the database, a first confidence interval threshold for a first predicted odor memory score;
  calculate, from a relationship between the score for the odor discrimination test and the plurality of previously-entered performance data, a second confidence interval threshold for a second predicted odor memory score;
  determine whether the score for the odor memory test is greater than the first confidence interval threshold and the score for the odor discrimination test is greater than the second confidence interval threshold; and
  responsive to a determination that the score for the odor memory test is not greater than the first confidence interval threshold and the score for the odor discrimination test is not greater than the second confidence interval threshold, generate a report, to be displayed by the at least one computing device, identifying a user as high risk for a neurodegenerative disease.

15. The non-transitory computer-readable storage media of claim 14, wherein the instructions include steps for administering an odor identification test that cause the computing device to:
  transmit an instruction to the olfactometer to deliver the odor;
  generate the user interface comprising:
    a cue that the odor will be delivered;
    an odor recognition user interface component;
    an odor selection user interface component comprising a plurality of odor selections;
  receive from the user, via the at least one user interface:
    a positive or negative response, via the odor recognition user interface component, indicating whether the user recognizes the odor;
    a selection, via the odor selection user interface component;
  query the database to identify a correct response for the selection;
  calculate the score for the odor identification test, wherein, if a correct response matches the selection, the score is increased, and if the correct response does not match the selection, the score is decreased.

16. The non-transitory computer-readable storage media of claim 14, wherein the instructions include steps for administering the odor memory test that cause the computing device to:
  transmit an instruction to the olfactometer to deliver the odor;
  generate the user interface comprising:
    a cue that the odor will be delivered;
    a previous odor recognition user interface component;
    an odor selection user interface component comprising a plurality of odor selections;
  receive from the user, via the at least one user interface:
    a positive or negative response, via the previous odor recognition user interface component, indicating whether the user recognizes the odor from the first odor delivered;
    a selection, via the odor selection user interface component;
  query the database to identify a correct response for the selection;
  calculate the score for the odor memory test, wherein, if a correct response matches the selection, the score is increased, and if the correct response does not match the selection, the score is decreased.

17. The non-transitory computer-readable storage media of claim 14, wherein the instructions include steps for administering the odor discrimination test that cause the computing device to:
    transmit an instruction to the olfactometer to deliver a first odor and a second odor from among the plurality of odors;
    generate the at least one user interface comprising:
        a cue that the first odor will be delivered;
        a cue that the second odor will be delivered;
        an odor discrimination user interface component;
    receive from the user, via the at least one user interface:
        a selection, via the odor discrimination user interface component, indicating whether the first odor and the second odor were the same or different;
    query the database to identify a correct response for the selection;
    calculate an odor discrimination score, wherein, if the correct response matches the selection, the score is increased, and if the correct response does not match the selection, the score is decreased.

18. The non-transitory computer-readable storage media of claim 14, wherein, prior to the olfactometer delivering the odor, the user interface comprises no indication of an expected odor.

19. The non-transitory computer-readable storage media of claim 14, wherein the computing device calibrates the first predicted odor memory score and the second predicted odor memory score according to the score for the odor memory test and the odor discrimination test.

\* \* \* \* \*

UNITED STATES PATENT AND TRADEMARK OFFICE
CERTIFICATE OF CORRECTION

| | |
|---|---|
| PATENT NO. | : 10,610,147 B2 |
| APPLICATION NO. | : 15/512541 |
| DATED | : April 7, 2020 |
| INVENTOR(S) | : Mark W. Albers |

It is certified that error appears in the above-identified patent and that said Letters Patent is hereby corrected as shown below:

In the Specification

Please insert the following after the first paragraph in Column 1, Line 3:
--STATEMENT REGARDING FEDERALLY SPONSORED RESEARCH
This invention was made with government support under OD000662 awarded by the National Institutes of Health. The government has certain rights in the invention.--.

Signed and Sealed this
Ninth Day of May, 2023

Katherine Kelly Vidal
*Director of the United States Patent and Trademark Office*